United States Patent
Cosentino, II

(10) Patent No.: US 9,579,155 B2
(45) Date of Patent: Feb. 28, 2017

(54) BOXED GLOVE DISPENSER

(71) Applicant: Michael J. Cosentino, II, Webster Groves, MO (US)

(72) Inventor: Michael J. Cosentino, II, Webster Groves, MO (US)

(*) Notice: Subject to any disclaimer, the term of this patent is extended or adjusted under 35 U.S.C. 154(b) by 0 days.

(21) Appl. No.: 14/468,111

(22) Filed: Aug. 25, 2014

(65) Prior Publication Data
US 2016/0051330 A1    Feb. 25, 2016

(51) Int. Cl.
*A61B 50/20*    (2016.01)
*A61B 19/04*    (2006.01)

(52) U.S. Cl.
CPC ............ *A61B 19/045* (2013.01); *A61B 42/40* (2016.02); *A61B 50/20* (2016.02)

(58) Field of Classification Search
None
See application file for complete search history.

(56) References Cited

U.S. PATENT DOCUMENTS

| 3,168,275 | A | * | 2/1965 | Grondin | A47K 10/185 |
| | | | | | 108/152 |
| 5,927,488 | A | * | 7/1999 | Gray | A24F 17/00 |
| | | | | | 206/237 |
| 2004/0099680 | A1 | * | 5/2004 | Mitchell | 221/45 |
| 2006/0027468 | A1 | * | 2/2006 | Berar | 206/210 |
| 2007/0181594 | A1 | * | 8/2007 | Thompson | 221/190 |
| 2011/0259908 | A1 | * | 10/2011 | Case et al. | 221/45 |
| 2011/0297692 | A1 | * | 12/2011 | Conway | A47K 10/185 |
| | | | | | 221/45 |
| 2012/0068027 | A1 | * | 3/2012 | Tyner | 248/201 |
| 2012/0298689 | A1 | * | 11/2012 | Cohen | 221/197 |
| 2013/0213989 | A1 | * | 8/2013 | Kimple et al. | 221/1 |

* cited by examiner

*Primary Examiner* — Gene Crawford
*Assistant Examiner* — Ayodeji Ojofeitimi
(74) *Attorney, Agent, or Firm* — Charles McCloskey

(57) ABSTRACT

A boxed glove dispenser has a front and an opposite back, two spaced apart ends connecting the front and the back, a top connecting the front, back, and ends, and a bottom opposite the top. The bottom has a lesser depth than the top and connects to the front and the back using two rails. The rails provide two edges parallel to the length of the dispenser and elevate a box placed upon the rails slightly above the bottom. The bottom also has a grate centered in it. The grate has a transverse orientation to the length of the bottom. The grate operates as an opening into the dispenser, yet the opening limits a medical provider's access within the dispenser to no more than two fingers while promoting single glove retrieval from any glove box placed within the dispenser.

1 Claim, 4 Drawing Sheets

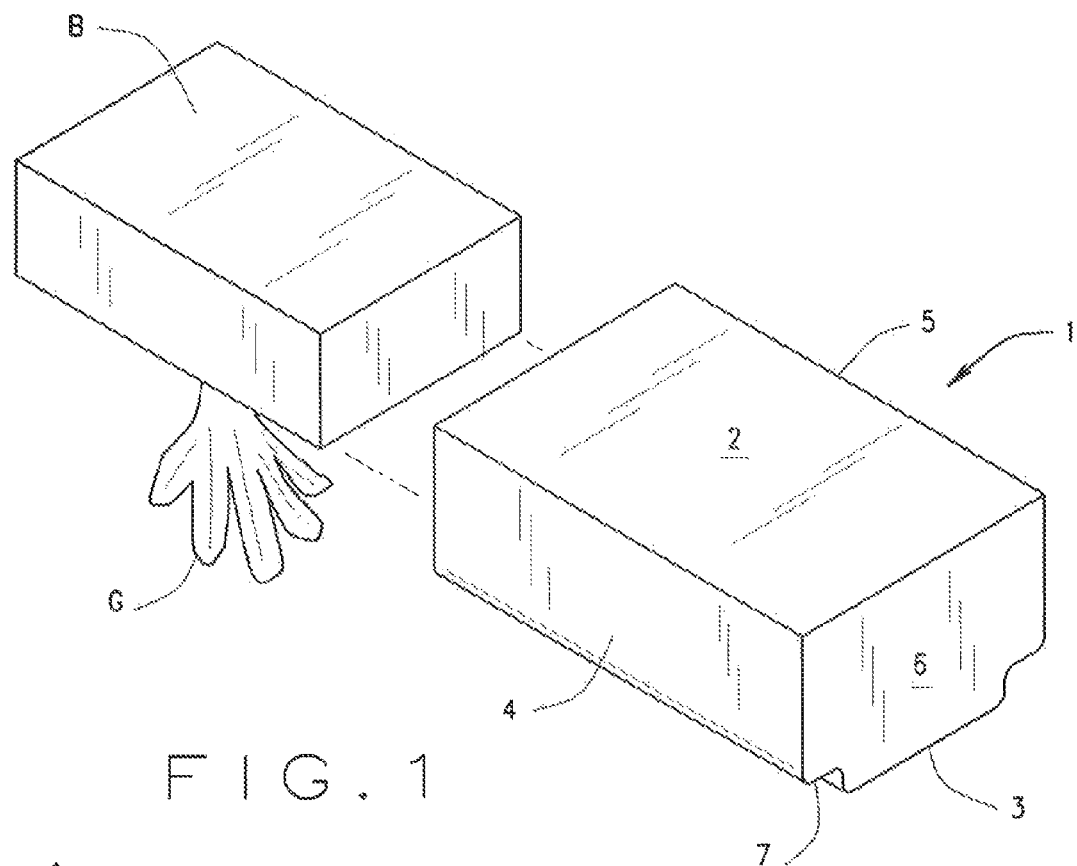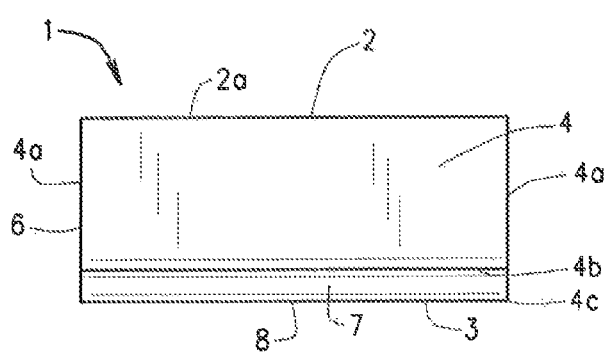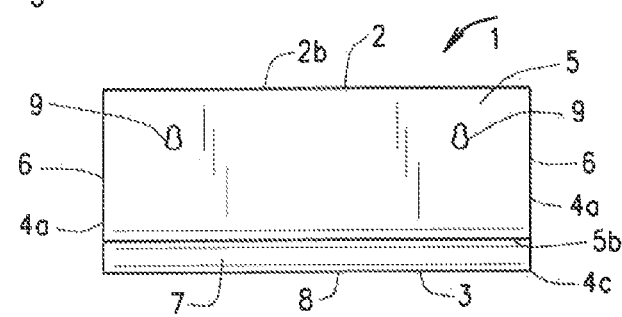

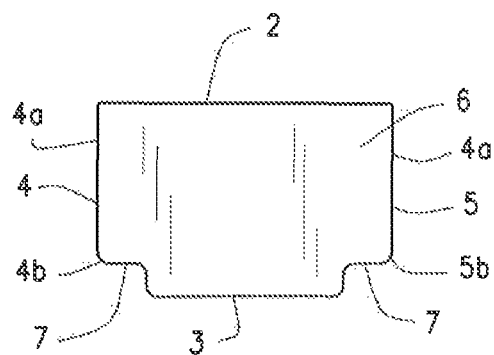
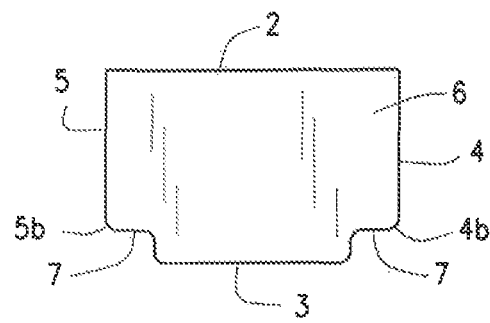
FIG. 4    FIG. 5
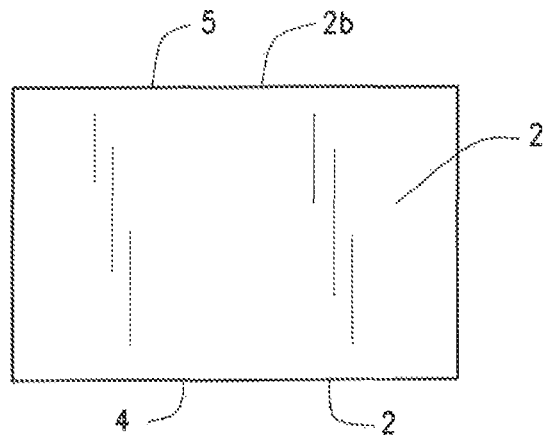
FIG. 6
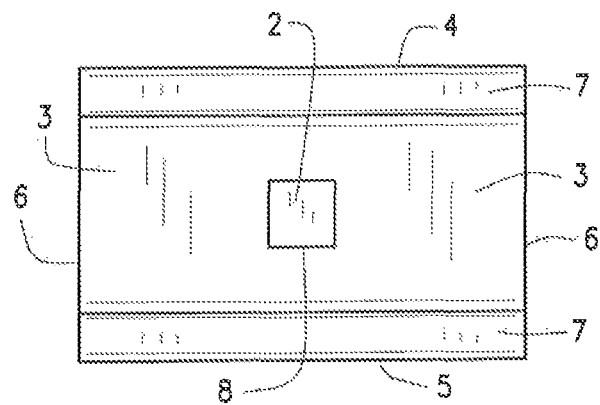
FIG. 7

BOXED GLOVE DISPENSER

BACKGROUND OF THE INVENTION

The boxed glove dispenser generally relates to dispensers of personal protective equipment and more specifically to a dispenser for gloves. The dispenser releases gloves singly under gravity feed.

Early on medical providers worked with the clothes on their backs and their bare hands. Such conditions led to germ transmission from doctor to patient, patient to doctor, other patient to doctor to patient, and the like. Morbidity and mortality from infection and transfection was a risk at every turn in a medical setting. Before the turn of the last century, William Halstead pioneered use of surgical gloves as a professor at Johns Hopkins University. From those humble beginnings at one medical school and many epidemiological studies later, gloves have become abundant in hospitals and medical settings of all kinds. Gloves come in many kinds, however examination gloves of various materials see prevalent use. Gloves see additional use in dental practices and is other locations where a service provider contacts a patient. Gloves generally prevent a provider from transmitting his own germs to a patient and the patient from transmitting germs back to the provider.

Medical providers now use gloves ubiquitously. Early training of medical providers, continuing training, and reminders from insurers, prompt and stimulate glove usage. The AIDS crisis of the 80s and 90s also reinforced the need to wear gloves. The appearance of MRSA in the 2000s and this decade also prompts usage of gloves. Medical providers generally have gloves in ample stock and readily available, typically in exam rooms and surgical suites among other places. Medical providers typically reach for a pair of gloves from a storage box and place them on their hands before contacting a patient.

Medical providers have such conditioned responses about gloves that they overlook what happens as they retrieve a pair of gloves. Retrieving gloves has its own problematic issues as further described.

DESCRIPTION OF THE PRIOR ART

For many years, a hospital, medical practice, dental practice, and the like received gloves in prepackaged boxes from the glove maker. The boxes were then placed upon a table or other flat surface and a medical provider lifted gloves from the box similar to people retrieving a tissue. Medical providers also placed glove boxes in various holders. The holders typically attached to a wall or other upright surface and positioned a glove box generally perpendicular to a floor, that is, parallel to the wall. A medical provider would then pull gloves outwardly from the box. Other holders retained the glove box within them and slightly downwardly from an access opening. A medical provider then reaches into the holder and down into the box to retrieve gloves upwardly. In this application, medical provider is to be viewed expansively and includes staff that holds a license, unlicensed staff, certified staff, users, and persons in medical, veterinary, and other practices that seek to minimize cross contamination and direct contact with patients in a multitude of settings.

While the prior art holders keep a glove box in place, the holders have little if any effect on waste of gloves and cross-contamination by users, or medical providers, touching gloves not yet used. Recent tests have found contamination on the gloves in the current glove holders from medical providers reaching into the box of gloves and touching, often unintentionally, more than one glove at a time. Microbiologists have identified this as a means for cross-contamination.

The prior art glove holders have the gloves facing outwardly, that is, towards medical providers. The prior art glove holders do little to prevent the gloves from falling out of their box or deterring a medical providers from touching many gloves inside the box. Other prior art glove holders utilize the packaging of the gloves for their dispensing. The packaging is often a grade of paperstock, such as paperboard, and susceptible to carrying contamination and acquiring contamination from medical providers. Also, the existing paperboard boxes have a large opening for retrieving gloves. Upon inverting an existing paperboard box, the gloves tend to fall from the box.

The present invention overcomes the disadvantages of the prior art and provides a boxed glove dispenser that allows users to touch only one glove at a time, and that prevents medical providers from reaching into and contaminating an entire box of gloves. The flaps then fold over a frame and secure to the bag utilizing an adhesive.

SUMMARY OF THE INVENTION

Generally, the boxed glove dispenser has structure and features that permit no more than an index finger and a thumb of one hand, or two adjacent fingers of one hand, to enter a glove storage box while each glove dispenses by gravity yet only allowing the user to touch the glove being dispensed. The dispenser has a generally rectangular, hollow prismatic form. The dispenser has a front and an opposite back, two spaced apart ends connecting the front and the back, a top connecting the front, back, and ends, and a bottom opposite the top. The bottom has a lesser depth than the top and connects to the front and the back using two rails. The rails provide two edges parallel to the length of the dispenser and elevate a box placed upon the rails slightly above the bottom. The bottom also has a grate centered in it. The grate has a transverse orientation to the length of the bottom. The grate operates as an opening into the dispenser, yet the opening limits a medical provider's access within the dispenser to no more than two fingers while promoting single glove retrieval from any glove box placed within the dispenser.

There has thus been outlined, rather broadly, the more important features of the invention in order that the detailed description thereof that follows may be better understood and that the present contribution to the art may be better appreciated. The present invention also includes these additional features.

The grate has a size for no more than thumb and forefinger access and permits access by a pair of adjacent fingers. The grate has a size that deters access by a whole hand or wrist of a user. The grate has a generally centered location so one glove dispenses. The grate has a design to cause just enough friction for single glove retrieval. If the grate has a width less than that of a glove aperture in a glove box, the grate could cause multiple gloves to tear. If the grate has a length similar to or exceeding that of the glove aperture, it causes too many gloves to fall from the dispenser. Because, the gloves automatically fall onto themselves, the gloves are retrieved one by one.

The grate has a position lowered from about 0.5 inches to about 2 inches below the glove box, so the box rests upon on side rails designed to lessen friction. The grate, beneath the base of the raised box, limits finger pinching into the box and reaching into box. The upward positioning of the box, that is, the lowered grate position relative to the box, prevents accumulation of friction by a glove box placed within the dispenser and by the gloves sitting directly on the grates.

The grate has a location at the bottom of the dispenser for glove retrieval as later shown in FIG. 1. The grate has its length generally perpendicular to the length of the dispenser and has an approximate length of about 1 inch to about 5 inches and an approximate width of about 0.5 inches to about 4 inches. The grate has a centered location upon the length of the dispenser's bottom so that one glove exits the glove box by itself, that is, without bringing the next glove down. Preferably, the grate has a square shape and alternatively it has a round, triangular, polygonal, or irregular shape.

The dispenser operates at an angular range from parallel to a horizon and thru a 45 degree angle to the horizon. The grate in cooperation with the orientation of the dispenser allows gloves to automatically fall through the dispensing grate singly, and only allowing one by one retrieval by a user.

The present invention dispenses a glove at a time and lets the user don a pair of gloves manually one by one.

Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a boxed glove dispenser that restricts access to only one glove at a time.

Another object is to provide such a boxed glove dispenser that reduces waste of gloves.

Another object is to provide such a boxed glove dispenser that reduces waste of gloves by over ten percent.

Another object is to provide such a boxed glove dispenser that delivers one glove with a single touch from a user.

Another object is to provide such a boxed glove dispenser that stands by itself.

Another object is to provide such a boxed glove dispenser that is manufactured at a price so the purchasing consumers, contractors, home centers, hardware stores, and other sales venues can readily purchase or offer the bag for sale.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying is drawings and descriptive matter in which there is illustrated a preferred embodiment of the invention.

BRIEF DESCRIPTION OF THE DRAWINGS

In referring to the drawings,
FIG. 1 is an isometric view of the invention to receive a box of gloves;
FIG. 2 is a front view of the invention;
FIG. 3 is a back view of the invention;
FIG. 4 is an end view of the invention;
FIG. 5 shows an end view opposite that of FIG. 4;
FIG. 6 provides a top view of the invention;
FIG. 7 illustrates a bottom view of the invention showing the grate.

The same reference numerals refer to the same parts throughout the various figures.

DESCRIPTION OF THE PREFERRED EMBODIMENT

Figure 8:
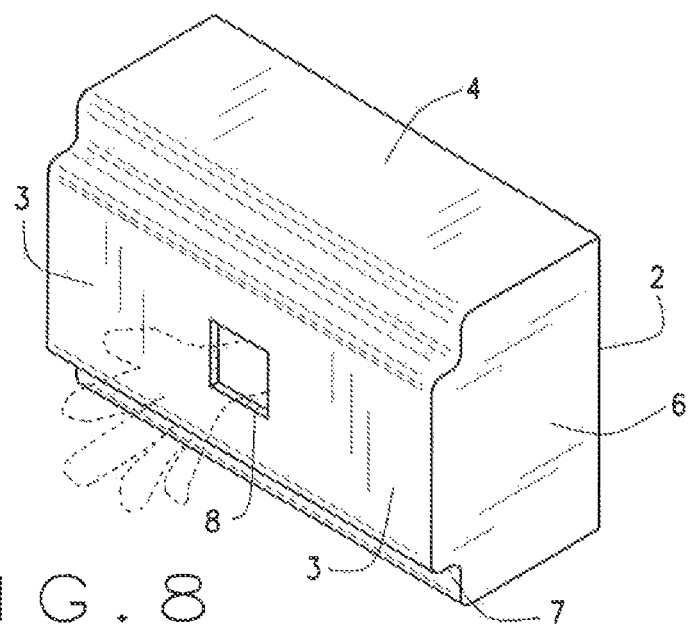
FIG. 8 shows a bottom perspective view.

The present invention overcomes the prior art limitations by providing a boxed glove dispenser. This dispenser limits retrieval of gloves from their box to one at a time upon pulling by a medical provider. Though this description refers to gloves in a medical setting, the invention may see use in a food related setting that requires gloves. FIG. 1 shows an invention or dispenser 1 that receives a box B of gloves G where the gloves G are made by others and packaged in the box B for shipment and eventual placement at a medical location. To place the box B into the dispenser, a medical provider removes the perforated cover from the opening manufactured into the box, then inserts the box B opening downwardly into the dispenser. This downward insertion is shown in FIG. 1 with a glove G depending from the box B towards the upper left of the figure. FIG. 1 shows the box prepared for insertion into an end of the dispenser 1. However, alternate ways of insertion of the box are foreseen.

The dispenser has a generally rectangular prismatic form that begins with a top 2, here shown as rectangular, and an opposite bottom 3 generally parallel to and spaced beneath the top. In FIG. 1, the bottom appears concealed but is shown later in FIG. 7. The bottom has a narrower width than the top. Depending from the top, a front 4 is mutually parallel and spaced apart from a back 5, not shown. The top has a longitudinal axis and a perpendicular lateral axis, where the longitudinal axis has a greater length than the lateral axis. The front 4 and the back 5 are parallel to the longitudinal axis of the top but perpendicular to a plane defined by the top. The front and the back have a height generally slightly more than the typical box B of gloves G. Perpendicular to the top 2, the front 4, and the back 5, the dispenser has two spaced apart ends 6. The two ends are mutually parallel and spaced apart. The ends have a height similar to that of the front and the back and have a width similar to the lateral axis of the top. Opposite the top, each end 6 has its width narrow along two spaced apart rails 7. The rails have an arcuate form when viewed on end as shown and transition the width of the end from its maximum to its minimum at the bottom 3. The rails extending inwardly into the dispenser and provide elevation or lift of the box B of gloves G above the bottom 3 as later shown.

FIG. 2 shows the dispenser 1 in a front view as a medical provider would see it. Though this description refers to medical provider, that term has an expansive use to include any user of gloves who cares for a patient. The dispenser has its top 2 that joins to its front 4 upon a front edge 2a. The front has its generally rectangular shape that has two spaced apart upright edges 4a where the ends 6 join to the front. The upright edges are generally perpendicular to the plane of the top. The front and its upright edges descend to a forward edge 4b generally parallel to the front edge 2a. The forward edge 4b represents the upper and outer limit of a rail 7. The rail has a concave, hollow form that curves inwardly and downwardly from the forward edge 4b to the inward front edge 4c. The inward front edge 4c then joins to the bottom 3.

Centered upon the rail 7 and the bottom 3, a grate 8 has a generally square shape in a central position between the front 4 and the back 5. The grate is an opening in the bottom with two of its four edges parallel to the rails. The grate though has a width that only admits two fingers along both axes of the square shape of the grate. In an alternate embodiment, the grate is rotated 45 degrees into a diamond like shape with no edges parallel to the rails. In a further alternate embodiment, the grate has a round shape, a triangular shape, a polygonal shape, an irregular shape, and the like. The key part of the grate's shape restricts medical providers to only inserting two fingers.

Opposite the front 4, FIG. 3 shows the back 5 mutually parallel and spaced apart from the front 4. The back 5 joins to the top upon a back edge 2b. The back is also rectangular in shape of similar proportions as the front. The back also has two spaced apart upright edges 4a where the ends 6 join to the back. The back also has two hanging holes, keyhole in shape, as at 9. The Applicant foresees other hanging mechanisms may substitute for the incised hanging holes. The dispenser 1 also installs upon a supporting surface, such as a wall, at an angle of up to and including 45 degrees. Two chocks, generally triangular in shape prop and rotate the dispenser to a desired angular orientation, that is, with the grate 8 tipped upwardly and rotated towards the supporting surface. This orientation allows gravity to assist dispensing of gloves singly from within a box within the dispenser.

These upright edges 4a also have a generally perpendicular orientation to the plane of the top. The back and its upright edges descend to a rear edge 5b generally parallel to the back edge 2b. The rear edge 5b represents the upper and outer limit of the other rail 7. This rail has a concave, hollow form that curves inwardly and downwardly from the rear edge 5b to an inward rear edge 5c. The inward rear edge 5c then joins to the bottom 3 mutually parallel and spaced apart from the inward front edge 4c. This rail is generally a mirror image of the rail joined to the front 4.

As in FIG. 2, FIG. 3 shows the grate 8 has its generally square shape centered between the front 4 and the back 5. The grate opens through the bottom with two of its four edges parallel to the rails. The grate's width though only admits two fingers of a medical provider along both axes of the square shape of the grate such a width is a key part of the invention.

Turning the dispenser to its shorter face, FIG. 4 shows an end 6 of the dispenser 1. The end 6 begins with its joining to the top 2 generally parallel to the lateral axis of the top, that is, the shorter dimension of the top. The end then continues downwardly along the upright edges 4a to the front 4 and the back 5. Where the upright edges stop away from the top, the rails 7 join to the front 4 and the back 5 with the forward edge 4b and the rear edge 5b respectively. The rails then mutually transition inwardly and downwardly to the bottom 3. The bottom has a lesser width than the top as shown. However, the width of the rails when combined with the width of the bottom equals the width of the top, making for an overall rectangular form to the shorter dimension of the dispenser.

The present invention is generally symmetric. FIG. 5 shows the opposite is end 6 of the dispenser. The rails 7 do extend from one end 6 to the other end 6 of the dispenser.

Turning the dispenser upwardly, FIG. 6 shows the top 2 of the dispenser. As mentioned in FIG. 1, the top has a generally rectangular form with a longitudinal axis having a length that exceeds the lateral axis. The top joins to the front 4 upon the front edge 2a and the back upon the back edge 2b. The front edge and the back edge are mutually parallel and spaced apart. Perpendicular to the front edge and the back edge, the lateral axis shows the ends 6 joining to the top 2. The front, the back, and the ends mutually depend downwardly from the top.

FIG. 7 then illustrates a bottom view of the invention as what a medical provider would see when looking upwardly to the invention. This figure has the bottom 3 in the foreground, that is, opposite FIG. 6. The bottom appears with the grate 8 centered upon it, dividing the bottom into left, right, front, and back portions. The grate is a sized opening penetrating the bottom. In an alternate embodiment, the grate extends slightly into the rails 7. As before, the grate is generally centered upon the bottom and has edges parallel to the length of the dispenser, that is, the longitudinal axis of the top. The opening of the grate 8 reveals a lower surface of the top 2 in the background. The bottom extends outwardly and joins to the rails 7 and the grate 8 remains centered in the bottom and spaced away from the rails. The rails then extend outwardly to the forward edge 4b and the rear edge 5b of the front 4 and the back 5 respectively.

The grate has a width, along the width of the dispenser as a medical provider sees it from the front from left to right, no larger than the greater of a person's thumb and forefinger when adjacent or forefinger and middle finger. This width deters a medical provider from inserting additional fingers into the box B of gloves G and contaminating the remaining gloves in the box. The grate has a length, transverse the width of the dispenser, no larger than the length of the bottom from the front to the back, and preferably smaller. This length allows for fit and positioning of a box B of gloves G within the dispenser. In an alternate embodiment, the length is reduced to about that of the width of the grate, effectively a square opening.

Turning the dispenser from its position in FIG. 7, FIG. 8 shows a bottom perspective view of the dispenser ready to dispense a single glove G to a medical provider. The dispenser 1 has its rectangular form with the front 4, top 2, ends 6, and bottom 3 as before. The rails 7 extend inwardly and downwardly from the forward edge 4b and the rear edge 5b as before to the bottom 3 with its narrower width than the top 2. The bottom also includes the grate 8 centered in it. The grate leaves an opening of appropriate size in the bottom and a location between the rails 7 spaced inwardly from where the rails flatten for later acceptance of a box B.

Figure 9:
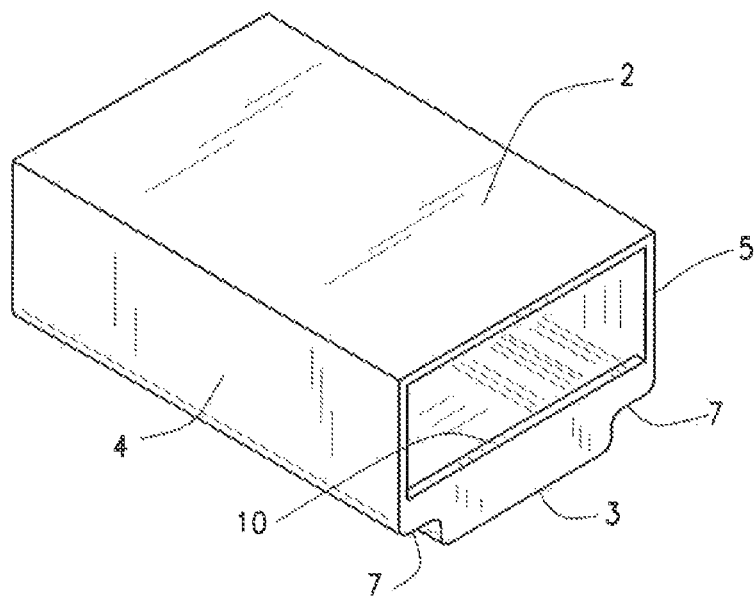
FIG. 9 shows an end view of an alternate embodiment.

FIG. 9 shows an alternate embodiment of the dispenser with respect to the ends. In this alternate embodiment, the ends are replaced with stops 10. Each stop has a clipped rectangular shape with two corners recessed inwardly that follow the path of the ends of the rails. The stop then extends slightly above the rails, typically less than 2.1 inches. The stop also spans the edge of the bottom similar to as the ends 6 had done. The stop has an inverted hat shape. Above the stop, the dispenser remains open for insertion of a box B within the dispenser. In a further alternate embodiment, the back edge 2b of the top is replaced with a hinge and the front edge 2a of the top is free from a joint to the top. The hinge includes appropriate mounting and closing hardware.

Figure 10:
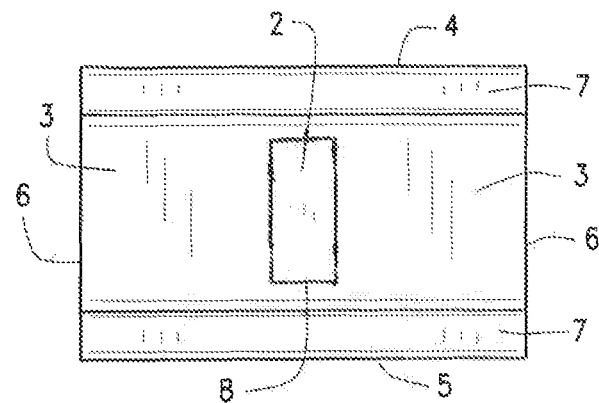
FIG. 10 shows a bottom view of an alternate embodiment particularly of the grate; and,
FIG. 11 shows an end view of an alternate embodiment with chocks.

In a further alternate embodiment, the grate 8 has a generally rectangular shape transverse between the front 4 and the back 5 as shown in FIG. 10. The rectangular grate opening shows a lower surface of the top as at 2. The grate is generally hollow and perpendicular to the rails 7. The grate opens at the inward front edge 4c widens slightly above that edge and has a somewhat partial elliptical shape as shown. The grate then ends at an elevation above the bottom, typically where the rail abuts a box B when placed within the invention.

Figure 11:
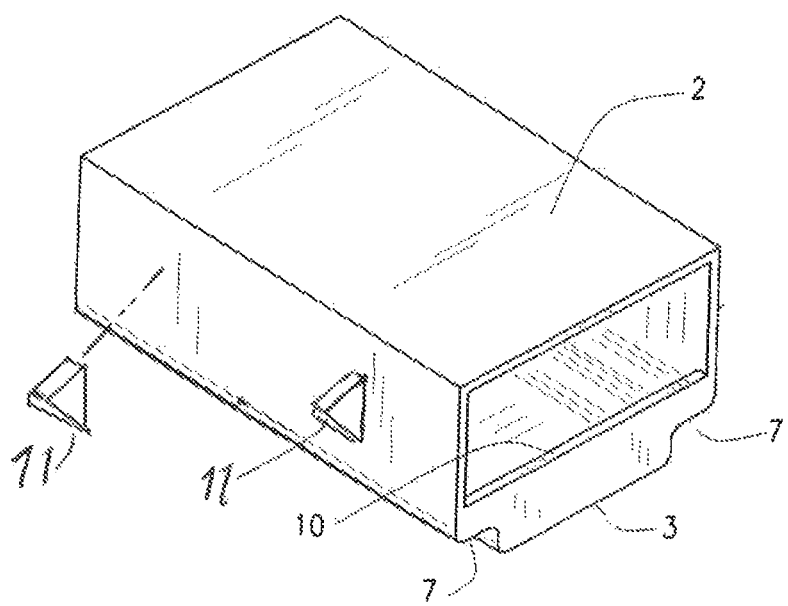

And, FIG. 11 shows a perspective view of the back with two chocks 11 attached. The chocks have a generally triangular shape that positions the back at up to a sixty five degree angle from a supporting surface, such as a vertical wall, not shown in a medical or other setting that calls for gloves. Each chock has its triangular shape with at least one internal angle up to sixty five degrees. The internal angle sets the angled orientation of the dispenser to the supporting surface. The dispenser permits retrieval of gloves singly up to an including an angle of sixty five degrees.

The dispenser has an embodiment with a planar bottom, the bottom having a width and a perpendicular length less than the width. It has also a grate transverse the bottom where the grate has a width parallel to that of the bottom and a length of the grate perpendicular to the grate's width. Two rails, generally continuous, mutually parallel and spaced apart join to the bottom outwardly of the grate and each rail has a height above the bottom from about 0.1 inches to about 3 inches. Continuing the form of the dispenser, a front joins to one of said rails, the front being perpendicular to the bottom and a back joins to the other of rail, the back being perpendicular to the bottom and parallel the front. Two mutually parallel and spaced apart ends join to the front, the back, the bottom and the rails. A top has a position mutually parallel to and spaced above the bottom and a width greater than the bottom. The rails receive a box of gloves, centering it upon the grate, and elevating the box permitting its deflection above the grate. The dispenser restricts a user to gripping only one glove at a time with two fingers.

The grate typically has four edges, each of them being ninety degrees to an adjacent next edge. Often two of the edges are parallel to the rails. Following the square opening of the grate in FIG. 7, the edges each have the same length and the rails have a continuous shape. Each rail has a spacing above the bottom beneath the front and the back. The back has an alternate embodiment to suspend the dispenser at up to a sixty five degree angle from a supporting surface such as a vertical wall. The angle of the back arises from at least one chock having a triangular shape and an internal angle up to sixty five degrees. The chocks position between the back and a supporting surface to put the device into an angled orientation. In an alternate embodiment, the grate has an opening of select forms such as round, triangular, or polygonal. The grate has an opening along its narrowest dimension, or width, from about 0.5 inches to about 4 inches and along its longest dimension, or length, from about 0.5 inches to about 5 inches.

Another alternate embodiment has the top hingedly connected to the back along the edge 2b. Though previous embodiments have described two rails, the dispenser may also support a box of gloves using supports placed between the bottom and the front and the back. The supports, likely two towards the front and one towards the back, provide minimum stability for a box of gloves yet elevate the box above the bottom from about 0.1 inches to about 3 inches. The supports also center the box of gloves and permit the box of gloves, or a supply of gloves to bend a little as a user removes one glove from the supply. The supports can be as small as single bosses or small prismatic rectangles so long as the supply of gloves can rest upon the supports.

From the aforementioned description, a boxed glove dispenser has been described. The boxed glove dispenser is uniquely capable of The boxed is glove dispenser also The boxed glove dispenser and its various components may be may be manufactured from many materials, including but not limited to, paper, kraft paper, paperstock, paperboard, cardboard, burlap, steel, aluminum, polymers, ferrous and non-ferrous metal foils, their alloys, and composites.

Various aspects of the illustrative embodiments have been described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations have been set forth in order to provide a thorough understanding of the illustrative embodiments. However, it will be apparent to one skilled in the art that the present invention may be practiced without the specific details. In other instances, well known features are omitted or simplified in order not to obscure the illustrative embodiments.

Various operations have been described as multiple discrete operations, in a manner that is most helpful in understanding the present invention, however, the order of description should not be construed as to imply that these operations are necessarily order dependent. In particular, these operations need not be performed in the order of presentation.

Moreover, in the specification and the following claims, the terms "first," "second," "third" and the like—when they appear—are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A device to dispense a supply of gloves one at a time to a user, said device having a form suitable to hold the supply of gloves, wherein the improvement comprises:
- a planar bottom, said bottom having a width and a perpendicular length less than said width;
- a grate transverse said bottom, said transverse grate having a width parallel to said width of said bottom and a length of said transverse grate perpendicular to said width of said transverse grate;
- at least two supports, mutually spaced apart, joining to said bottom outwardly of said transverse grate, each of said supports extending inwardly and upwardly from said transverse grate towards the interior of said dispensing device;
- wherein said supports are adapted to receive the supply of gloves, adapted to center the supply of gloves above said transverse grate, and adapted to elevate the supply of gloves permitting its deflection proximate said transverse grate;
- two mutually parallel and spaced apart ends, each of said ends joining to said front, said back, said bottom and said supports, each of said ends having a stop extending slightly above said supports and leaving an opening bounded by said stop, said supports, said front, and said back, said opening being coplanar with said stop, said opening being perpendicular to said transverse grate in a plane defined by said bottom;
- wherein said device is adapted to allow a user to grip only one glove at a time with two fingers through said transverse grate; and,
- wherein said transverse grate is adapted to deter insertion of more than two human adult fingers into said device.

* * * * *